(12) United States Patent
Gassner et al.

(10) Patent No.: US 9,011,405 B2
(45) Date of Patent: Apr. 21, 2015

(54) INCONTINENCE ARTICLE IN PANT FORM

(71) Applicant: Paul Hartmann AG, Heidenheim (DE)

(72) Inventors: Oliver Gassner, Ulm (DE); Andreas Beyrle, Nattheim (DE); Rüdiger Kesselmeier, Herbrechtingen (DE); Krzysztof D. Malowaniec, Heidenheim (DE)

(73) Assignee: Paul Hartmann AG, Heidenheim (DE)

( * ) Notice: Subject to any disclaimer, the term of this patent is extended or adjusted under 35 U.S.C. 154(b) by 181 days.

(21) Appl. No.: 13/896,559

(22) Filed: May 17, 2013

(65) Prior Publication Data

US 2013/0324957 A1    Dec. 5, 2013

Related U.S. Application Data

(60) Provisional application No. 61/659,442, filed on Jun. 14, 2012.

(30) Foreign Application Priority Data

May 18, 2012    (DE) .......................... 10 2012 208 394

(51) Int. Cl.
*A61F 13/496*    (2006.01)
*A61F 13/49*    (2006.01)

(52) U.S. Cl.
CPC . *A61F 13/49017* (2013.01); *A61F 2013/49036* (2013.01); *A61F 13/49011* (2013.01); *A61F 13/49019* (2013.01); *A61F 13/4902* (2013.01); *A61F 13/49061* (2013.01); *A61F 13/4963* (2013.01); *A61F 2013/49026* (2013.01); *A61F 2013/49028* (2013.01)

(58) Field of Classification Search
CPC .......................... A61F 13/49019; A61F 13/539
See application file for complete search history.

(56) References Cited

U.S. PATENT DOCUMENTS

| | | | |
|---|---|---|---|
| 7,993,320 B2 | 8/2011 | Hornung et al. | |
| 8,100,173 B2 | 1/2012 | Hornung et al. | |
| 2004/0133181 A1* | 7/2004 | Ishiguro et al. | 604/385.28 |
| 2004/0186453 A1 | 9/2004 | Shimada et al. | |
| 2005/0107764 A1 | 5/2005 | Matsuda et al. | |
| 2006/0025746 A1 | 2/2006 | Sasaki et al. | |
| 2007/0293833 A1* | 12/2007 | Wennerback | 604/385.01 |
| 2009/0178755 A1 | 7/2009 | Hornung et al. | |
| 2011/0040277 A1 | 2/2011 | Rajala et al. | |
| 2011/0112500 A1* | 5/2011 | Wenzel et al. | 604/385.3 |
| 2011/0144611 A1* | 6/2011 | Saito | 604/385.14 |

(Continued)

FOREIGN PATENT DOCUMENTS

| | | |
|---|---|---|
| DE | 102007055628 | 5/2009 |
| DE | 102007063209 | 6/2009 |

(Continued)

*Primary Examiner* — Susan Su
(74) *Attorney, Agent, or Firm* — Henry M. Feiereisen LLC

(57) ABSTRACT

In an incontinence article in pant form, a longitudinal extent of respective lateral seams is 100-170 mm, a ratio between this extent and an extent of the incontinence article between a waist border and a transverse center axis of the incontinence article is at most 0.42, wherein first elastifying means have a distance to one another which is at least 20% greater than a distance between second elastifying means to one another defined in the lateral seam region of the incontinence article, wherein the first elastifying means have a thread strength which is at least 20% greater than a thread strength of the second elastifying means, wherein the first and second elastifying means are fixed in the stomach section and in the back section with a pre-tension, and wherein the pre-tension of the first elastifying means is at least 10% greater than the pretension of the second elastifying means.

24 Claims, 9 Drawing Sheets

(56) References Cited

U.S. PATENT DOCUMENTS

2011/0288517 A1* 11/2011 Mori .................... 604/385.3
2012/0078213 A1    3/2012 Nakaoka et al.

FOREIGN PATENT DOCUMENTS

| | | |
|---|---|---|
| EP | 0 988 145 | 4/2004 |
| EP | 1 867 311 | 12/2007 |
| EP | 2 371 334 | 10/2011 |
| JP | 2008-253289 A | 4/2004 |
| JP | 2006-204673 A | 12/2007 |
| JP | H11-36103 A | 6/2009 |
| JP | 2007-082890 A | 10/2011 |
| WO | WO 2011/098226 A1 | 8/2011 |
| WO | WO 2011/105475 A1 | 9/2011 |

* cited by examiner

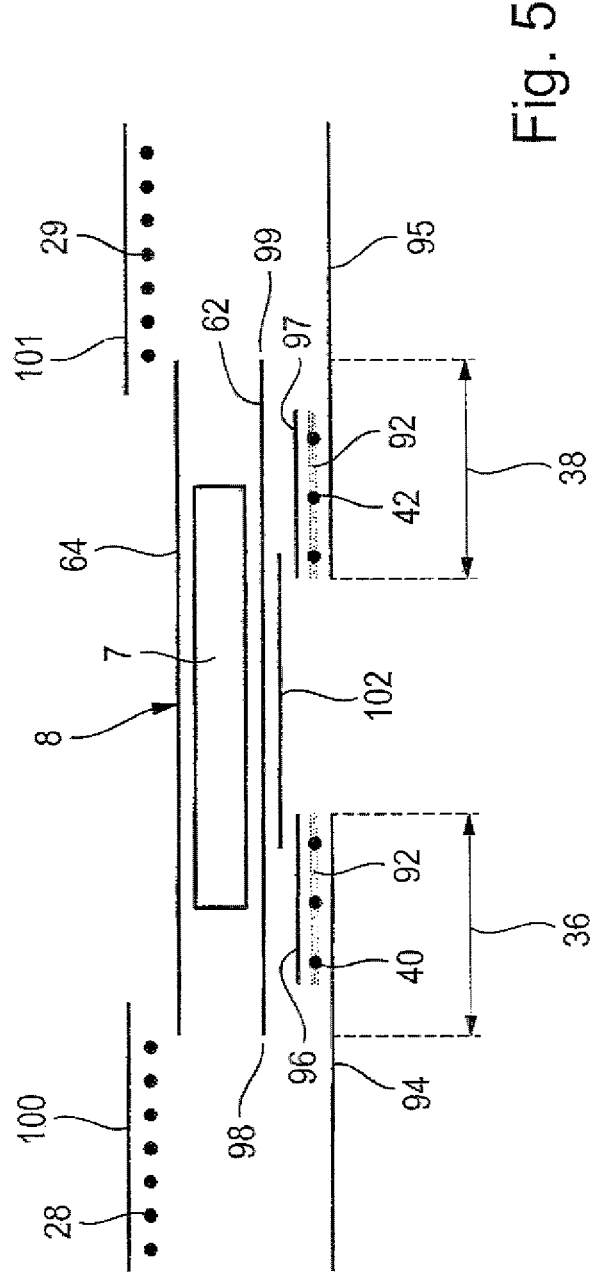

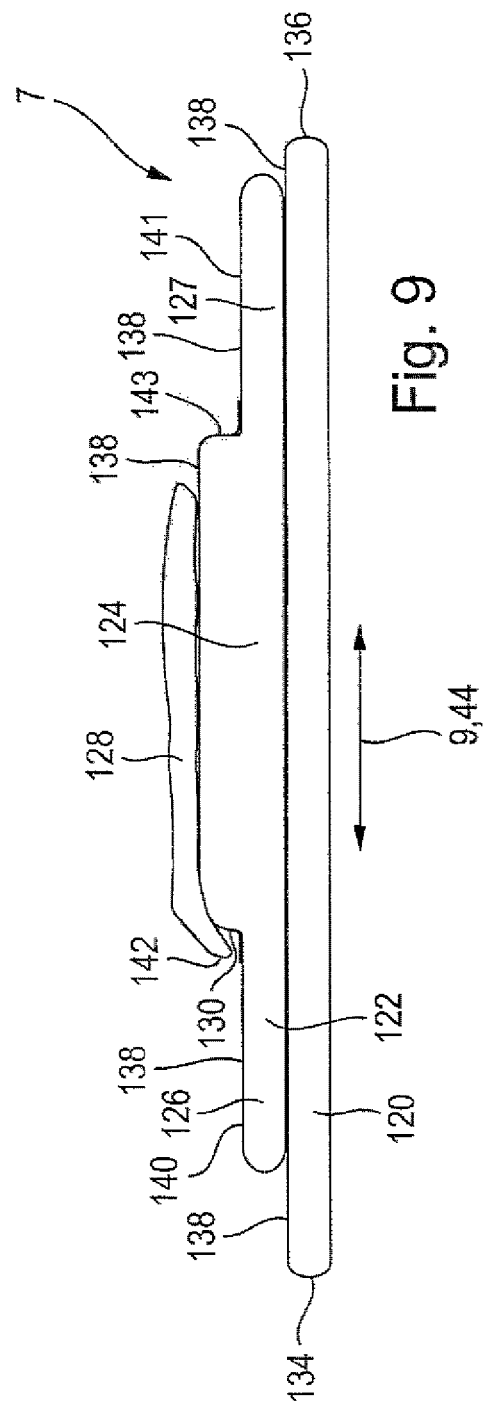

INCONTINENCE ARTICLE IN PANT FORM

CROSS-REFERENCES TO RELATED APPLICATIONS

This application claims the benefit of prior filed U.S. Provisional Application No. 61/659,442, filed Jun. 14, 2012, pursuant to 35 U.S.C. 119(e), the disclosure of which is incorporated herein by reference.

This application claims the priority of German Patent Application, Serial No. 10 2012 208 394.4, filed May 18, 2012, pursuant to 35 U.S.C. 119(a)-(d), the disclosure of which is incorporated herein by reference.

BACKGROUND OF THE INVENTION

The present invention relates to an incontinence article in pant form.

The following discussion of related art is provided to assist the reader in understanding the advantages of the invention, and is not to be construed as an admission that this related art is prior art to this invention.

Incontinence articles in pant form principally differ from openable and closable incontinence articles in conventional diaper form, in that the waist circumference is already predetermined by the pant form, and the adjustment to different body sizes based on a number of basic sizes is achieved in that the article can be elastically stretched. For this, elastifying means, in particular in the form of bands or threads, often also referred to as Lycra—bands are usually connected to chassis materials of the incontinence article in a pre-tensioned state (Stretch-Bond-Method) i.e., they are fixed in a pre-tensioned state on the chassis materials for example by means of glue. Due to their pre-tension, these elastifying means bundle chassis materials together, thereby forming plications, which typically extend transverse to the direction in which the elastifying means are pre-tensioned, i.e. in this case in longitudinal direction of the article. The incontinence article or the elastified chassis materials of the incontinence article can then be elastically stretched again when the user puts on the incontinence article like a pant. The chassis materials themselves on the other hand are preferably non-elastic and can thus be guided in a well defined manner in the transport plane in a flat or evenly spread out state so that the elastifying means can then be attached with a defined pre-tension.

In known incontinence articles of the type discussed here, there is a tendency to configure the stomach section and the back section and with this the stomach- or back band which is formed by them and is continuous in waist-circumferential direction relatively expansive, so that the waistband or waist border comes to lie relatively high on the user. This has the purpose to create a relatively great body-contacting surface of the stomach- and back band, which is two-dimensionally elastified over its extent, which surface alone determines and maintains the fit of the incontinence article on the body of the user. The greater the body-contacting and elastified surface of the stomach section and back section, the greater are the forces which hold the incontinence article on the body. After all, it has to be insured that the incontinence article does not slide down when used in the customary, intended manner.

At the starting point of the present invention, it was recognized that a broad stomach- and back band i.e., a high positioned waist border or waistband is associated with the problem that the border region of the waistband of the incontinence article folds outwardly, especially in the case of mobile users and in a very pronounced manner in users with a paunch. In this case, folding over or rolling over by several centimeters can occur in longitudinal direction, resulting in a significant reduction of the body-contacting surface, whereupon the secure fit of the incontinence article is no longer ensured. In addition, this leads to a strong local increase of pinching forces acting in circumferential direction, because multiple elastifying means come to lie in a manner of speaking on one waist-circumferential line.

This leads to an unpleasant wearing experience, potentially involving severe skin irritations, but not to an improved fit of the hygiene article.

Significantly reducing the width or longitudinal extent of the stomach- and back band does also not lead to a satisfactory wearing situation, even though the problem of outward folding of the waist border can be reduced. However, pinching forces still occur and the elastification of the stomach- and back band cannot be solved satisfactorily.

It would therefore be desirable and advantageous to provide an incontinence article with an improved fit, and with this improved wearing comfort in an economically acceptable manner.

SUMMARY OF THE INVENTION

According to one aspect of the present invention, an incontinence article in pant form for absorbing bodily excretions, includes a stomach section, a back section, spaced apart from the stomach section in a longitudinal direction of the incontinence article along a longitudinal center axis, wherein the stomach section and back section have respective lateral seam regions and are joined at the respective lateral seam regions to form respective lateral seams extending in the longitudinal direction thereby forming a stomach- and back band which is continuous in a transverse direction of the incontinence article, and has a circumferentially closed waist opening; a crotch section having an absorption body and a body-averted side and extending in the longitudinal direction between the stomach section and the back section, wherein the crotch section overlaps with the stomach section and the back section in respective overlapping regions and is non-detachably connected with the body-averted side to the stomach section and to the back section in the respective overlapping regions, wherein the stomach section, back section and crotch section together delimiting leg openings of the incontinence article, wherein the stomach and back section have respective crotch-side regions facing the leg openings; first elastifying means extending in spaced apart and parallel relationship to one another in the transverse direction in the stomach section and back section, thereby two-dimensionally elastifying the stomach section and the back section; and second elastifying means extending in the respective crotch-side regions of the stomach and back sections, from the respective lateral seam regions towards the longitudinal center axis into the respective overlapping regions of the crotch section and back section and of the crotch section and stomach section in an arched course with increasing distance to one another, wherein an extent of the respective lateral seams in the longitudinal direction is 100-170 mm, and wherein a ratio between the extent of the respective lateral seams in longitudinal direction and an extent of the incontinence article between a waist border of the stomach- and back band and a transverse center axis of the incontinence article is at most 0.42, wherein in the stomach section and in the back section a ratio between a distance of an outermost, waist-facing one of the first elastifying means in the longitudinal direction to an innermost, crotch-facing one of the first elastifying means and the extent of the incontinence article between a border of the waistband and the transverse center axis is at most 0.3, wherein the first elastifying means have a distance to one another which is at least 20% greater than a distance between the second elastifying means to one another defined in the lateral seam region, wherein the first elastifying means have a thread strength which is at least 20% greater than a thread strength of the second elastifying means, wherein the first and second elastifying means are fixed in the stomach section and in the back section with a pre-tension, and wherein the pre-tension of the first elastifying means is at least 10% greater than the pretension of the second elastifying means.

According to the invention, it is thus proposed to configure the stomach- and back band which is continuous in transverse or waist-circumferential direction and is formed by the stomach section and the back section narrower, so that the border of the stomach- and back band comes to lie lower at the user in longitudinal direction of the body of the standing user. In order to compensate for the thereby reduced planar extent of the stomach section and the back section, the number of elastifying means is not increased but in the contrary, the distance of the first elastifying means to each other is selected greater than in the second elastifying means. In this way, the number of the first elastifying means is significantly reduced, which at the same time improves the economic efficiency of the hygiene article. According to the invention, it was also recognized that this reduction of the planar extent and the reduction of the number of the elastifying means through increase of the distance of the first elastifying means to each other does not lead to disadvantages, as long as the return force of a respective first elastifying means is increased, by using a greater thread strength and a stronger pre-tension for the first elastifying means when introducing and fixing the first elastifying means. Preferably, a greater thread strength as well as a greater pre-tension is used. The pre-tension is defined as the degree of stretching of the stretched elastifying means relative to the non-stretched/relaxed original state of the elastifying means in the state of applying and fixing the elastifying means in the manufacturing machine. The degree of stretching is thus calculated as the ratio between the stretched length L' (=starting length L+ΔL) and the starting length L, i.e., L'/L.

The thread strength of the elastifying means is expressed in the unit dtex (1 dtex=1 g/10,000 m). The thread strength is determined according to the testing provisions BISFA, the International Bureau for the Standardization of man-made Fibres, Test methods for bare elastane yarns, edition 1998, chapter 5: "Determination of linear density". The thread strength or linear density is determined by determining the mass of a test specimen having a known thread length of 1,000 mm (cut under a standard pre-tension of 0.1+/−0.01 mN/dtex) after a conditioning under standard conditions (23° C.+/−2° C., 50%+/−5% relative humidity) in the relaxed state.

The thread strength (in dtex) is calculated from the quotient of the mass (in g) divided by the length of the section (in m) multiplied by the factor 10,000.

For this, five sections of the thread-shaped or band-shaped elastifying means having a length of 1,300 mm are cut off from the role or package under smallest possible tension, in uneven distances of at least 2 m. These five sections are relaxed so as to be tension-less and are let rest under standard conditions for at least four hours. Then, a test specimen of 1,000 mm+/−1 mm is cut off from the respective 1,300 mm long section, while the section is maintained under a pretension of 0.1 mN/dtex. The cut off test specimens of 1,000 mm length are weighed to an accuracy of +/−1% of their expected mass. For each testing specimen, its thread strength is obtained by multiplying the respective mass with the factor 10,000 in dtex. From the five test specimen, the arithmetic mean value is calculated which is used as thread strength for the purposes discussed here.

For determining the extent L1 of the incontinence article between border of the stomach- and back band and the transverse center axis, the transverse center axis is defined so that the longitudinal extent of the incontinence article in the stretched out, flattened out state is divided into two identical subsections during guidance in the flat-material tracks in the manufacturing machine (FIG. 7). The total length of the diaper is thus 2×L1. All remaining dimensions mentioned here also refer to the flat, stretched out state of the flat materials shown in FIG. 1.

In typical sizes, the longitudinal extent L1 of the incontinence article discussed here is 320 to 450 mm, in particular 330 to 440 mm and further in particular 340 to 430 mm.

As mentioned, the first elastifying means essentially extend in transverse—or waist-circumferential direction. The second elastifying means extend—as mentioned—also starting from a respective lateral seam region in the direction towards the longitudinal middle axis; along their course they fan out and extend more or less arch-like, wherein the arch-shape initially curves in the direction towards the transverse center axis, as can be well seen from FIG. 1. The distance of the second elastifying means to each other in a respective lateral seam region is about 3 to 8 mm. Further inwardly, in the direction towards the longitudinal center axis and in particular in the region of a border of an absorption body, the distance of the second elastifying means to each other is between about 7 and 35 mm, in particular between 12 and 30 mm.

Advantageously, the second elastifying means extend in the overlapping region in transverse direction, at least in the region of the longitudinal center axis, and preferably also parallel to one another.

This fanning-out of the second elastifying means can also be quantitatively described in more detail. For example, the second elastifying means of the back section shown in FIG. 1 have a minimum distance of 3 to 8 mm to each other (distance between immediately neighboring elastifying means) and at a border of an absorption body or a longitudinal border of the crotch section have a maximum distance to one another (distance between immediately neighboring elastifying means) of 7 to 35 mm. A degree F. of the fanning-out can be defined as follows:

$$F=(A-B)/B*100\%.$$

Advantageously, this fanning-out degree is between 50 and 900%, in particular between 100 and 700%, and further in particular between 150 to 550%. Advantageously, the fanning-out degree is greater in the back section than in the stomach section. The variables A and B are defined as the distance of the in longitudinal direction outermost second elastifying means to the in longitudinal direction innermost second elastifying means (i.e., not the distance between immediately neighboring elastifying means) i.e., A as the maximum distance, in particular at the longitudinal border of the crotch section, and B as the minimum distance, in particular in the lateral seam region.

It is further advantageous when the ratio (L2/L1) between the extent (L2) of the respective lateral seam in the longitudinal direction and the extent (L1) of the incontinence article between a border of the stomach- and back band and a transverse center axis is at most 0.4, in particular at most 0.39, in particular at most 0.38 and further in particular at least 0.20, further in particular at least 0.25, further in particular at least 0.30. According to the invention, it was discovered that within these range limits a well functioning configuration of the incontinence article with regard to the here-discussed aspects can be created. It is further advantageous, when in the stomach section and the back section the ratio (L4/L1) between the distance (L4) of the outermost waist-facing first elastifying means in longitudinal direction to the innermost crotch-facing first elastifying means and the extent (L1) of the incontinence article between the border of the stomach- and back band and the transverse center axis is at most 0.29, and in particular at least 0.12, in particular at least 0.15, in particular at least 0.18.

An advantageous absolute value for the distance L4 of the outermost waist-facing first elastifying means in longitudinal direction to the innermost crotch-facing first elastifying means is at most 120 mm, in particular at most 110 mm, in particular at most 100 mm, in particular at most 90 mm and in particular at least 60 mm, in particular at least 70 mm, in particular 70-110 mm, in particular 70-100 mm, in particular 70-100 mm, in particular 70-90 mm.

Due to the leg openings, the stomach section and the back section do not have their maximum extent in the lateral seam region, but rather towards the center of the incontinence article where the crotch section is provided. It is advantageous, when the maximum extent (L3B) of the stomach section in the longitudinal direction is 135-260 mm, in particular 125-250 mm and/or the maximum extent (L3R) of the back section in the longitudinal direction is 200-320 mm, in particular 210-310 mm.

As noted before, the three-component concept of the hygiene article composed of stomach section, back section and a crotch section that connects the stomach section and the back section implies, that the tracks which form the stomach section and the back section are spaced apart from one another in the longitudinal direction. In this regard, it is advantageous when a minimum distance between the stomach section and the back section in longitudinal direction is 250-400 mm, in particular 270-400 mm, further in particular 300-390 mm.

According to another advantageous feature of the present invention, the ratio (L2/Q) between the extent (L2) of the respective lateral seam in longitudinal direction and the extent (Q) of the stomach section or the back section in transverse direction is at most 0.22, in particular at most 0.20, in particular at least 0.10, in particular at least 0.14.

In a similar manner, the value L4 can relate to the transverse extent of the stomach section or the back section. It is advantageous in this context when in the stomach section and the back section the ratio (L4/Q) between the distance (L4) of the outermost waist-facing first elastifying means in the longitudinal direction to the innermost crotch-facing first elastifying means and the extent (Q) of the stomach section or the back section in transverse direction is at most 0.15, in particular at most 0.14, in particular at most 0.13 and in particular at least 0.05 and further in particular at least 0.08, and further in particular at least 0.10.

It is particularly advantageous, especially with regard to an economical manufacturability of the incontinence article, when the number of elastifying means can be reduced. Thus, in the stomach section and/or in the back section, the ratio (d1/L4) between the distance (d1) of the first elastifying means to one another in the longitudinal direction and the distance (L4) of the outermost waist-facing first elastifying means in longitudinal direction to the innermost crotch-facing first elastifying means can be between 0.08 and 0.25, in particular between 0.09 and 0.20, in particular between 0.10 and 0.18. In absolute values, the distance (d1) of the first elastifying means to one another in longitudinal direction is at least 8 mm, in particular at least 10 mm, in particular 10-15 mm, in particular 11-14 mm, further in particular 12-13 mm. Preferably, the first elastifying means are spaced apart by a same distance.

In contrast, a minimum distance of the second elastifying means to each other in their point of origin in the lateral seam regions is 3 to 8 mm, in particular 3 to 7 mm, in particular 3 to 6 mm.

It is further advantageous when the first elastifying means have a distance to one another which is at least 30%, in particular at least 50%, in particular at most 200%, in particular at most 180%, in particular at most 150%, greater than the distance of the second elastifying means to each other in the lateral seam region.

According to another advantageous feature of the present invention, thread-shaped or band-shaped elastifying means such as rubber threads, polyetherpolyurethane threads or polyesterolyurethane threads, preferably elastic threads such as Lycra- or Spandex can be used as first and/or second elastifying means.

According to another advantageous feature of the present invention, the first elastifying means can have a thread strength which is at least 30%, in particular at least 50%, in particular at most 150%, in particular at most 130%, in particular at most 100% greater than the second elastifying means.

It is further advantageous when the thread strength of the first elastifying means is at least 1000 dtex, in particular at least 1100 dtex, in particular at least 1200 dtex, in particular 1200-1500 dtex, in particular 1200-1400 dtex.

According to another advantageous feature of the present invention, the thread strength of the second elastifying means can be 500-1100 dtex, in particular 600-thousand dtex, in particular 700-900 dtex.

According to another advantageous feature of the present invention, the first elastifying means can be fixed with a pre-tension which is greater by at least 20%, in particular at least 30%, in particular at most 100%, in particular at most 80%, in particular at most 60%, than the second elastifying means.

The first elastifying means are fixed relative to the chassis materials with a pre-tension of 3-8, in particular 3-7, in particular 4-7 and further in particular 4-6.

The second elastifying means on the other hand are fixed with a smaller pre-tension of 2-5, in particular 2.5-4.5, in particular 2.5-4, and further in particular 3-4 compared to the pre-tension of the first elastifying means.

The composite of elastifying means and chassis materials of the incontinence article according to the invention is preferably formed as follows: The second elastifying means are arranged and fixed between a chassis material layer, preferably made of a nonwoven, which forms the body-averted visible side of the stomach section or the back section, and a chassis material layer positioned inwardly relative to the other chassis material layer and made preferably of a nonwoven, wherein the inwardly located chassis material layer essentially does not extend over the associated overlapping region of the crotch section and the stomach section or crotch section and back section in a longitudinal direction of the incontinence article. This is the case when the overlap is at most several mm, in particular at most 8 mm, preferably at most 5 mm.

According to another advantageous feature of the present invention, the second elastifying means can be fixed in a glue bed between chassis material layers and/or the first elastifying means are fixed between chassis material layers with glue provided in single-strand application on the first elastifying means. Provision of the glue in single strand application in the region of the first elastifying means allows avoiding a stiffening of the upper transversely elastified waist-side region of the stomach—and back section. In addition, in this context it is especially important and advantageous, that the chassis material layers, which abut one another, are not fixed to one another over a continuous surface. They can thus detach from each other outside of the first elastifying means to which adhesive has been applied in single-strand application. In conjunction with the first elastifying means, a particularly esthetically pleasing and in addition very soft and flexible frill formation results. In conjunction with the greater distance of the first elastifying means to one another and a higher return force of a respective first elastifying means, which can be achieved by greater thread strengths and/or greater pre-tension, a pleating of the chassis materials in the region of the first elastifying means, which is higher or greater in a direction of thickness of the incontinence article, can be achieved. This also results in a good fit. However, it also leads to a better grip or grippability of the stomach—and back band, which has been reduced in height.

Due to the fact that the second elastifying means are preferably fixed in a continuous glue bed between chassis material layers, a laminate results in which the layers are interconnected over their entire surfaces. This facilitates the joining of the chassis materials with further components, because no undefined pleating is formed by materials, which are not fixed to each other. The fixing of the second elastifying means in a glue bed is thus advantageous especially with regard to the joining of the crotch section with the stomach section or the back section, since the front and rear overlapping region of crotch section and stomach section or back section is located in the region in which the second elastifying means extend.

According to another advantageous feature of the present invention, the first elastifying means in the stomach section and in the back section are fixed between a body-averted chassis material layer and a body-facing chassis material layer by individually applying adhesive to the strands, and the body-facing chassis material layer protrudes over or overlaps the associated longitudinal end of the crotch section on the body-facing side of the crotch section. In this way, a material transition between the longitudinal end of the crotch section and the stomach section or back section which is unpleasant for the user can be avoided or covered, so that skin irritations can be avoided.

According to another advantageous feature of the present invention, the first elastifying means in the stomach section and in the back section can be fixed between a body-averted chassis material layer and a body-facing chassis material layer by single-strand application of adhesive to the first elastifying means, wherein on the border of the waist, none of the chassis material layers is folded about the other one, and the body-facing chassis material layer and the body-averted chassis material layer are not fixed to each other along the waist opening on the border of the stomach- and back band, so that they form a respective free-ending waist-side border section. This free-ending waist-side border section then corresponds in a manner of speaking to the distance between the outermost waist-facing first elastifying means and the geometric border. This border section measures in longitudinal direction preferably at least 4 mm, in particular at least 5 mm, in particular at most 15 mm, in particular at most 12 mm and further in particular at most 10 mm. This increases the softness of the border of the stomach- and back band, which extends in circumferential direction, which is perceived as pleasant by the user.

The chassis-forming materials of the stomach section and/or back section preferably include nonwoven materials such as spunbonds, card webs or through-air-bonded card webs. Particularly preferably, the chassis-forming materials of stomach section and/or back section include a spunbond material. The nonwoven materials that are used for the stomach section and/or back section preferably have a mass per area of 10-30 g/m$^2$, further preferably of 15-25 g/m$^2$. Particularly preferably, the stomach section and the back section include a spunbond, in particular made of polypropylene, in particular with a mass per area of 15-25 g/m$^2$. Low masses per area of the chassis forming materials of stomach section and/or back section, in particular including or being made of nonwoven materials due to their flexibility enable especially advantageously the formation of skin friendly structures.

The crotch section advantageously includes a liquid-impermeable back sheet material and a nonwoven topsheet-material. The backsheet-material includes in particular a film, in particular having a mass per area of 8-20 g/m$^2$, in particular of 8-16 g/m$^2$, in particular of 8-14 g/m$^2$. In particular, the backsheet includes a foil, which is in particular micro-porous and liquid tight during use but at the same time breathable and permeable for water vapor.

The absorption body includes materials, which absorb bodily fluids such as natural and synthetic fibers, in particular cellulose fibers, preferably in the form of cellulose fluff. Preferably, the absorption body further includes superabsorbent materials (SAP), in particular on the basis of surface cross-linked, partially neutralized polyacrylates.

According to another advantageous feature of the present invention, the surface of the overlapping region of crotch section and stomach section in relation to the surface of the stomach section can be at least 20%, in particular 20-35%, in particular 20-30% and/or when the surface of the overlapping region of crotch section and back section is at least 25%, in particular 25-45%, in particular 25-40%, in particular 27-40% of the surface of the back section.

The portion of the surface of the crotch section of the protected total surface of the stretched out incontinence article is preferably 30 to 60%, in particular 30 to 50%.

BRIEF DESCRIPTION OF THE DRAWING

Other features and advantages of the present invention will be more readily apparent upon reading the following description of currently preferred exemplified embodiments of the invention with reference to the accompanying drawing, in which:

FIG. 5 shows a schematic sectional view of the relevant individual components of the chassis materials along the longitudinal center axis of the incontinence article;

FIG. 9 shows a schematic longitudinal sectional view of the absorption body taken along the longitudinal center axis;

DETAILED DESCRIPTION OF PREFERRED EMBODIMENTS

Figure 1:
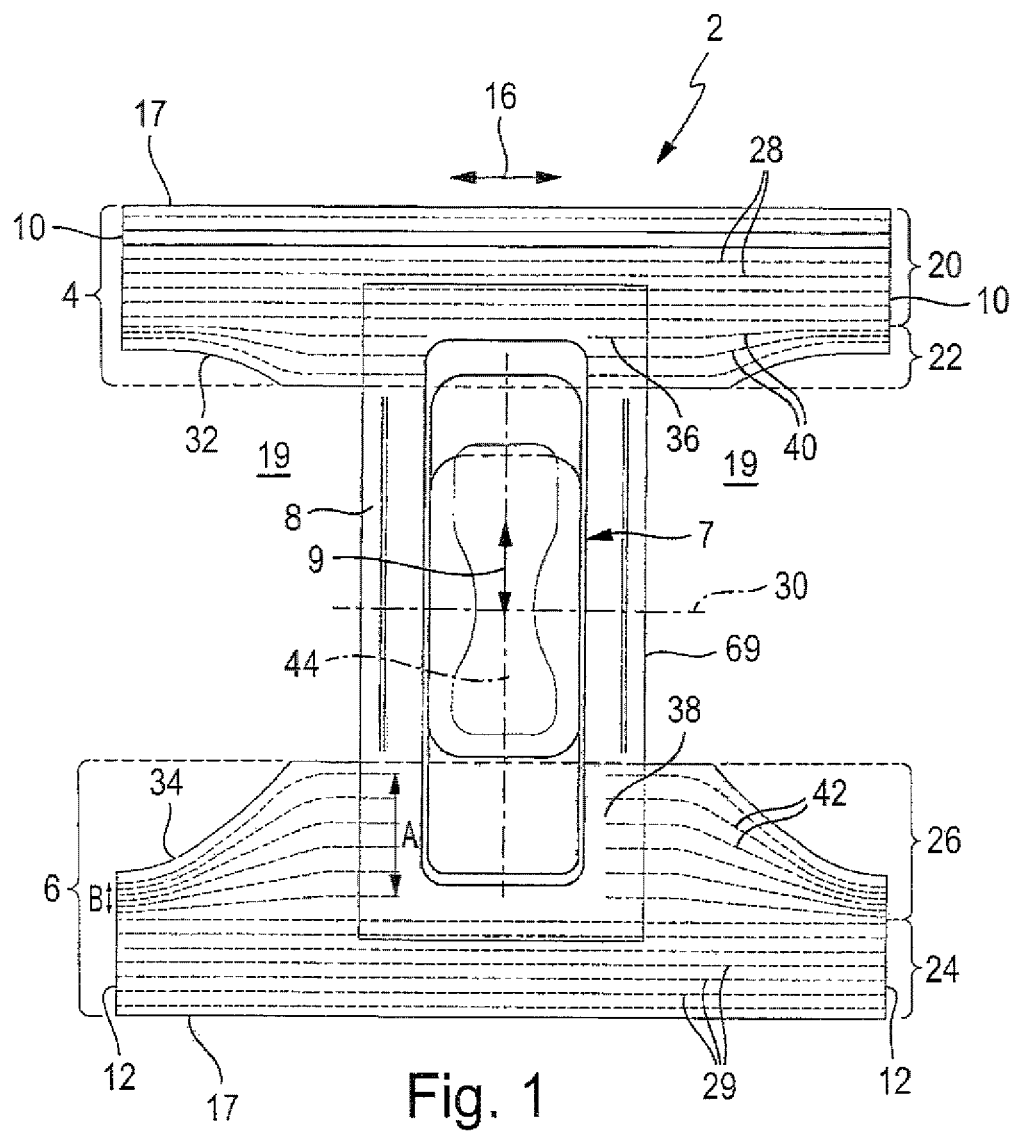
FIG. 1 shows a top view onto an incontinence article according to the invention, wherein a stomach section, a back section and a crotch section of the incontinence article are not yet joined for forming a pant form but are shown in a spread out and evenly stretched out state.

Throughout all the Figures, same or corresponding elements are generally indicated by same reference numerals. These depicted embodiments are to be understood as illustrative of the invention and not as limiting in any way. It should also be understood that the drawings are not necessarily to scale and that the embodiments are sometimes illustrated by graphic symbols, phantom lines, diagrammatic representations and fragmentary views. In certain instances, details which are not necessary for an understanding of the present invention or which render other details difficult to perceive may have been omitted.

The Figures show an incontinence article in pant form, overall designated with the reference numeral 2, for absorbing solid and liquid bodily excretions. The incontinence article 2 is composed of three components which can essentially be manufactured independently i.e., a front stomach section 4, a rear back section 6, and a crotch section 8 which has an absorption body 7 and is located between the stomach section 4 and the back section 6, wherein the crotch section 8 extends in a longitudinal direction 9 of the incontinence article 2 and overlaps with a substantial surface portion of the stomach section 4 on one hand, and of the back section 6 on the other hand, and is non-detachably connected by the manufacturer in the overlapping region in a manner to be described in more detail below. As can be seen from FIG. 1, this leads to an H-shaped basic structure of the incontinence article. For forming the pant form, the interconnected components shown in FIG. 1 are then connected to one another at respective lateral longitudinal border sections 10, 12 of the stomach section 4 and the back section 6, also by the manufacturer, by conventional joining methods, thereby forming lateral seam regions 14 on both sides. In this pant form of the incontinence article, which is manufactured by the manufacturer, the stomach section 4 and the back section 6 extend in a transverse- or waist-circumferential direction 16 continuously and thus define with their waist border 17 a waist opening 18 which is closed in waist-circumferential direction; further, together with the crotch section 8 they delimit leg openings 19, through which the user can put on the incontinence article like a pant.

The stomach section 4 can be divided into a waist-side region 20 and into a crotch-side region 22, which faces the leg openings 19. The back section 6 can be divided correspondingly i.e., also in a waist-side region 24 and a crotch-side region, which faces the leg openings 19.

In the waist-side region 20 of the stomach section 4 and in the waist-side region 24 of the back section 6, first elastifying means 28, 29 are provided, which may be Lycra-threads, and which are connected with the flat materials (chassis materials) of the stomach section 4 and the back section 6 in the so-called stretch-bond-method. These first elastifying means 28, 29 extend in transverse- or waist-circumferential direction 16 from one lateral seam region 14 to the other.

The respective crotch-side sections 22 and 26 of the stomach section 4 or of the back section 6 which face the leg openings 19 each have a border contour 32 or 34 which deviates from the transverse- or waist-circumferential direction 16 and which extends towards a transverse center axis 30 of the crotch section 8. This border contour 32, 34 is also arch-shaped in the representation according to FIG. 1 and therefore suited for delimiting the leg openings 19.

Through this extent of the crotch-side region 22 or 26 which faces the leg openings, a relatively great overlapping region 36, 38 between the crotch section 8 and the stomach section 4 or back section 6 is realized, which is important with regard to a tear-resistant connection of crotch section 8 and stomach section 4.

The respective crotch-side region 22, 26 of the stomach section 4 or the back section 6 which crotch-side region 22, 26 faces the leg openings 19, is also configured elastified and is provided with second elastifying means 40 or 42. The second elastifying means 40, 42 extend, in each case starting from the lateral seam regions 14, in the direction towards a longitudinal center axis 44 of the incontinence article. As can be seen from FIG. 1, the second elastifying means 40, 42 fan out in the direction towards the longitudinal center axis 44, i.e., with increasing distance to one another in the direction towards the longitudinal center axis 44. The second elastifying means 40, 42 pass underneath the crotch section 8. In the region below the absorption body 7, they may be deactivated i.e. they may not posses their elastifying effect.

Figure 2A:
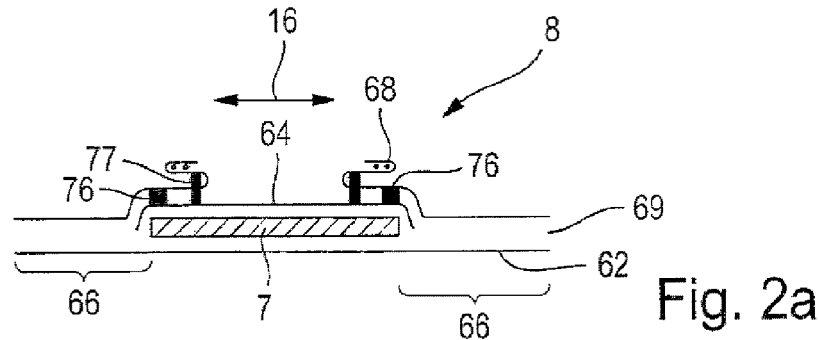
FIGS. 2 *a, b* show schematic sectional views of the crotch section in the region of the transverse centerline or in the overlapping region of crotch section and back section.
Figure 2B:
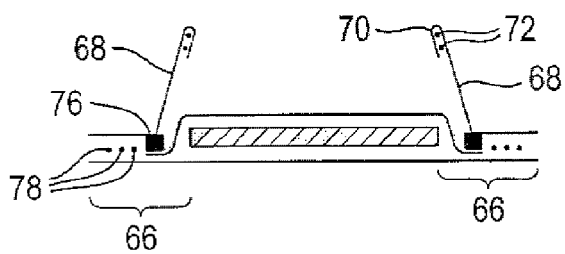

As can be seen from FIGS. 2 a, b, the crotch section 8 includes a liquid-impermeable backsheet material 62, which can in particular be formed by a breathable, but liquid-tight foil material and a preferably nonwoven-based topsheet material 64. The absorption body 7 (only shown schematically) is arranged between the backsheet material and the topsheet material. In the exemplary shown case, the backsheet material 62 forms an overhang 66 over the absorption body 7 in transverse direction 16. The topsheet 64 protrudes over the absorption body 7 in transverse direction 16 only to a relatively small degree and an upright barrier means 68 is provided on both sides of the absorption body 7. The barrier means 68 extends in a longitudinal direction 9, and is typically referred to as upright cuff element and is preferably made of a hydrophobic, in particular liquid-impermeable nonwoven material which extends in transverse direction 16 as far as to lateral longitudinal borders 69 of the crotch section 8. The distal ends 70 of the barrier means 68 are provided with further elastifying means 72 which raise the barrier means 68 during use of the incontinence article relative to the skin surface of the user. The lateral barrier means 68 are fastened on the topsheet 64 or onto themselves in a C-shape-folded configuration via schematically indicated fixations 76, 77. Outside of the absorption body 7 i.e., in the region of the protrusion 66, leg-elastifying means 78 are provided, which preferably extend at a defined distance to the material-rich and with this rather bending stiff absorption body 7, in order on one hand, to prevent exerting additional stretching or distortion forces on the absorption body, which might negatively influence the absorption properties of the absorption body and on the other hand to realize a liquid-tight leg sealing, which to the most degree is not influenced by the absorption body. These leg-elastifying means 78 end in longitudinal direction 9 at a significant distance of in particular 10 mm, preferably at least 20 mm before the second elastifying means 40 and 42 of the stomach section 4 or the back section 6. Preferably, these leg-elastifying means 78 end in longitudinal direction 8 before the stomach section 4 and the back section 6.

Figure 4:
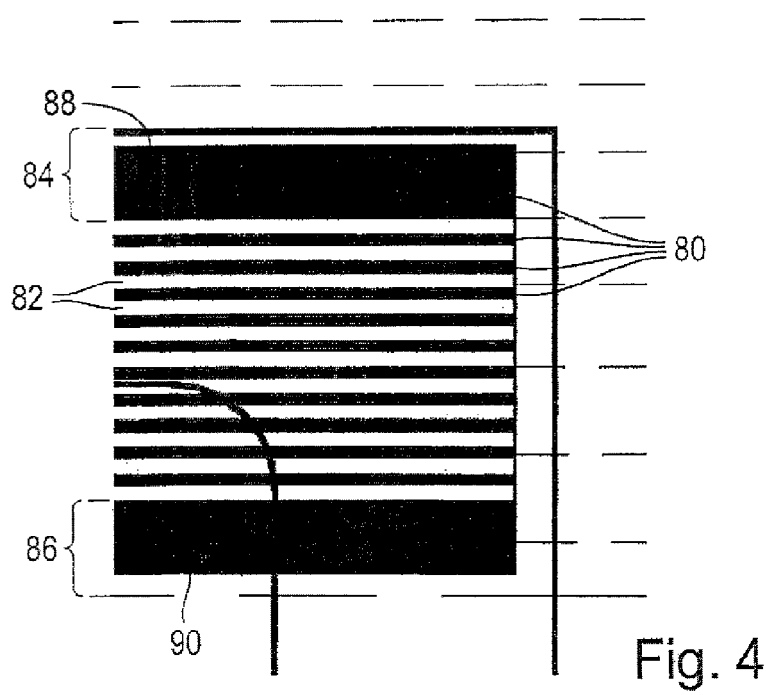
FIG. 4 shows an enlarged representation of a section in the region of the overlapping region of crotch section and stomach section or crotch-section and back section of the incontinence article according to FIG. 3.
Figure 3:
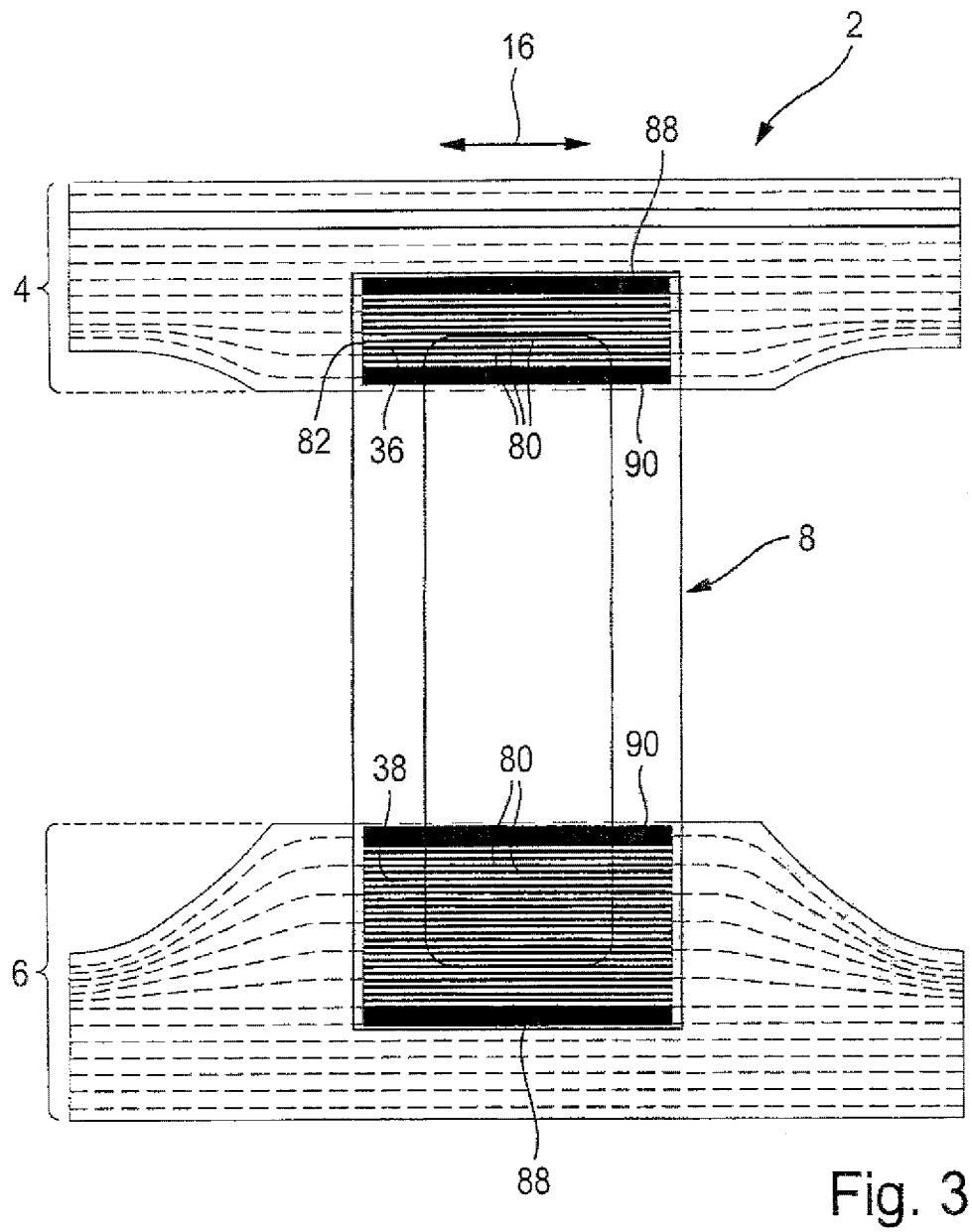
FIG. 3 shows a representation corresponding to FIG. 1, illustrating the fixing of the crotch section with the stomach section and the back section by means of adhesive strips.

In the following, the fixing of the crotch section 8 in the front overlapping region 36 with the stomach section 4 and in the rear overlapping region 38 with the back section 6 is described. As can be seen in FIGS. 3 and 4, for this purpose, adhesive is not applied to the entire surface, but multiple adhesive strips 80 are provided in the overlapping region and extend in transverse direction 16 and parallel to one another and are spaced apart by adhesive-free strips 82. The adhesive strips 80 occupy or overlap essentially the entire respective overlapping region 36, 38. In the exemplary shown, however, not strictly required case, broader adhesive strips 88 and 90 are provided in a border region 84 and a border region 86 of the respective overlapping region 36, 38, which border region 84 is located waist-side in longitudinal direction and which border region 86 faces away from the waist in longitudinal direction. The respective border-side i.e., waist-facing and waist-distal adhesive strips 88, 90 have a greater width than the multitude of adhesive strips 80 which are located inwardly and between the adhesive strips 88, 90. In an exemplary embodiment, the width of the border-side adhesive strips 88, 90 transverse to their extent is 14 mm, the width of the inwardly located adhesive strips 80 is 2 mm and the width of the adhesive-free strips 82 is 3 mm. In the exemplary and preferred shown case, the inwardly located adhesive strips 80 preferably all have the same width and the distances between them i.e., the width of the adhesive free strips 82 are preferably also the same. Nevertheless, the same explanations set forth in the beginning apply with regard to the dimensions and the conditions described there, as well as with regard to the mass per area of the adhesive coating of the adhesive strips. The surface of the front and rear overlapping region 36, 38 relative to the surface of the stomach section 4 or the back section 6 also lies within the previously explained preferred ranges.

It can further be seen from FIG. 3 in conjunction with FIG. 1 that the second elastifying means 40, 42 in the respective overlapping region 36, 38 extend parallel to the adhesive strips 80. In the exemplary shown case, some of the first elastifying means 28 also extend in the front and rear overlapping region 36, 38 (however on the body-facing side of the crotch section). The second elastifying means 40, 42 were also introduced so as to be continuous in the transverse direction 16; they are de-elastified in the respective overlapping region 36, 38 by the aforementioned measures. Even though the second elastifying means remain visible also in the de-elastified state—as explained above, they are concealed by the multitude of adhesive strips 80, thereby reducing their visibility.

In the preferred shown case, the second elastifying means are fixed in a glue bed 92 between chassis material layers 92 and 96 or 95 and 97 (c.f. FIG. 5). The glue bed 92 is applied on one of the chassis material layers 94, 96 or 95, 97. Then, the second elastifying means 40, 42 are placed on or introduced preferably in an endless manner and covered and laminated by the further chassis material layer. In this way, the second elastifying means 40, 42 are fixed and the chassis material layers 94 and 96 or 95 and 97 are joined to each other over their entire surfaces. The body-averted chassis material layer 94, 95 is a breathable fiber nonwoven material, which corresponds to the extent of the stomach section 4 or back section 6. The chassis material layer 96, 97 is an inwardly located fiber nonwoven material which is recessed relative to the chassis material layer 94, 95. In the preferred shown case, it ends in longitudinal direction 9 before the longitudinal end 98, 99 of the crotch section 8.

In the exemplary and preferred shown case, the first elastifying means 28, 29 are fixed between the body averted chassis material layer 94 or 95 and a further body-facing chassis material layer 100, 101 by single-strand application of adhesive. The further chassis material layer 100, 101 is again formed by a nonwoven material. The body-averted and the body-facing chassis material layers are exclusively interconnected by the first elastifying means 28, 29 to which adhesive has been individually applied i.e., only along the extent of these first elastifying means 28, 29. The skin friendly nonwoven materials are therefore not fixed to one another over their entire surfaces, but can detached from one another and, in particular as a result of the elastifing effect, can form pleatings and cuffs. In the preferred shown case, the body-facing chassis material layer 100, 101 extends in the stomach section 4 as well as in the back section 6 over the respective longitudinal end 98, 99 of the crotch section 8 on its body facing-side. It thus overlaps this material transition and in this way prevents an unevenness that leads to skin irritation.

Further, it can be seen in FIG. 5 that the backsheet 62 of the crotch section 8 has a coating 102 on its body-averted side. This coating 102 is a fiber nonwoven coating of the substantially liquid-impermeable backsheet 62. The coating 102 extends in longitudinal direction 9, however, not over the entire longitudinal extent of the backsheet 62 but instead ends relatively short within the front and rear overlapping region 36, 38. Outside of the overlapping region, the coating 102 is provided over the entire extent of the body-averted side of the back sheet 62. The coating 102 is preferably composed of a nonwoven material, in particular of a spunbond material, in particular of polypropylene, in particular with a mass per area of 10-20 g/m$^2$, in particular of 12-17 g/m$^2$.

Figure 6:
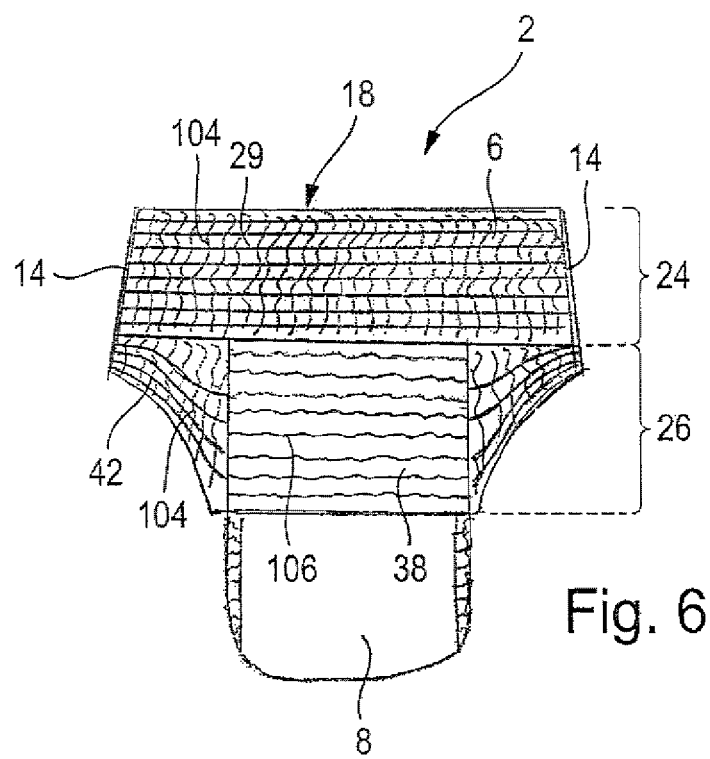
FIG. 6 shows a schematic view of the incontinence article in its final configuration.

FIG. 6 shows a schematic view of an incontinence article according to the invention in the finished configured state in which the stomach section 4 and the back section 6 are joined to one another, forming lateral seam regions 14. Only schematically shown are pleatings or cuffs 104 formed as a result of the contracting effect of the first and second elastifying means 28, 29, 40, 42, resulting from the fixing of the elastifying means in the pre-tensioned state on the chassis materials (stretch bond method). As a result of the multitude of relatively fine adhesive strips 80 in the respective overlapping region 36, 38 of crotch section 8 and stomach section 4 or back section 6, a visually and/or tactilely perceivable structure 106 is formed in the outer visible side of the incontinence article in the respective overlapping region 36, 38 which is here only shown as outline. According to the invention, it was found that the adhesive applied in strip-shape enters into the three-dimensional porous and also breathable configured fiber nonwoven materials, which are typically used as chassis materials, and leads to such an optical and/or tactilely perceivable structure 106, which can be advantageous as mentioned before. In addition, the connection of the crotch section 8 and stomach section 4 or back section 6 by the multitude of relatively narrow adhesive strips 80 leads to a very cost-effective use of adhesive while at the same time nevertheless providing the required holding forces for securely joining the three components to one another.

Figure 7:
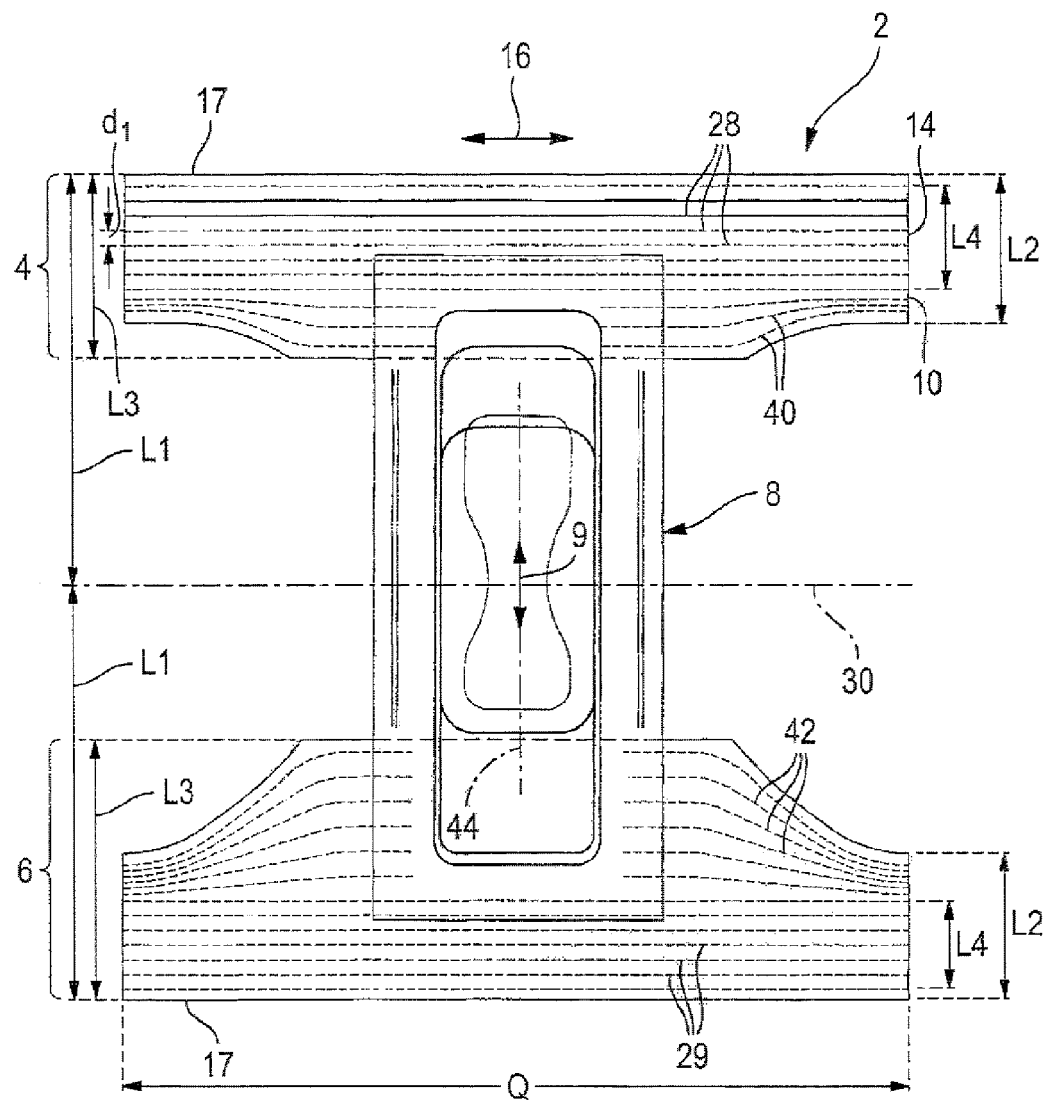
FIG. 7 shows a representation corresponding to FIG. 1, illustrating dimensions.

FIG. 7 explains the measurements, dimensions and ratios of the incontinence article according to the invention. It can be seen that the position of the transverse center axis 30 divides the overall length of the incontinence article in half in the flatly spread out state (according to FIG. 1). The transverse center axis 30 also forms a first folding axis 16 which extends in transverse direction 16, and about which the components are folded inside the manufacturing machine in order to arrange the longitudinal border sections 10, 12 of the stomach section 4 and back section 6 on top of one another for fixing and forming lateral seam regions 14 on both sides. Typically, this occurs by guiding endless, flat materials, which form the respective stomach section 4 and back section 6 i.e., even before the separation of the articles. The length L1 between the transverse center axis 30 and the respective border of the waist 17 can be seen. Further, the extent L2 of the respective lateral seam or the lateral seam region 14 in longitudinal direction 9 can be seen, which also corresponds to the length of the respective longitudinal border section 10 at 12. According to the invention, the ratio L2/L1 is at least 0.42.

Further, the distance L4 of the outermost waist-facing first elastifying means 28, 29 in longitudinal direction 9 to the innermost crotch-facing first elastifying means 28, 29 can be seen. According to the invention, the ratio L4/L1 is at most 0.3.

It can further be seen, that the first elastifying means 28, 29 have a distance d1 to one another, which is at least 20% greater than the distance of the second elastifying means 40, 42 to one another defined in the lateral seam region 14. In the preferred shown case, the first elastifying means 28, 29 all have the same distance d1 to one another, which is at least 10 mm, in particular 10 to 15 mm. The ratio d1/L4 is preferably 0.08 to 0.25.

Further, L3 can be seen as the extent of the stomach section 4 and back section 6 in longitudinal direction 9, which for the stomach section 4 is in particular 135-260 mm and for the back section 6 in particular 200-320 mm.

Further shown is the extent Q of the stomach section 4 or the back section 6 in transverse direction 16, which enters into ratios L2/Q or L4/Q.

The first elastifying means 28, 29 have a thread strength, which is at least 20% greater than the thread strength of the second elastifying means 40, 42. In addition, the first elastifying means 28, 29 are fixed with a pre-tension with the chassis material layers in the stomach section 4 and in the back section 6, which pretension is 10% greater than that of the second elastifying means.

Reference is made to the further preferred afore described measurements, dimensions and ratios.

Figure 8:
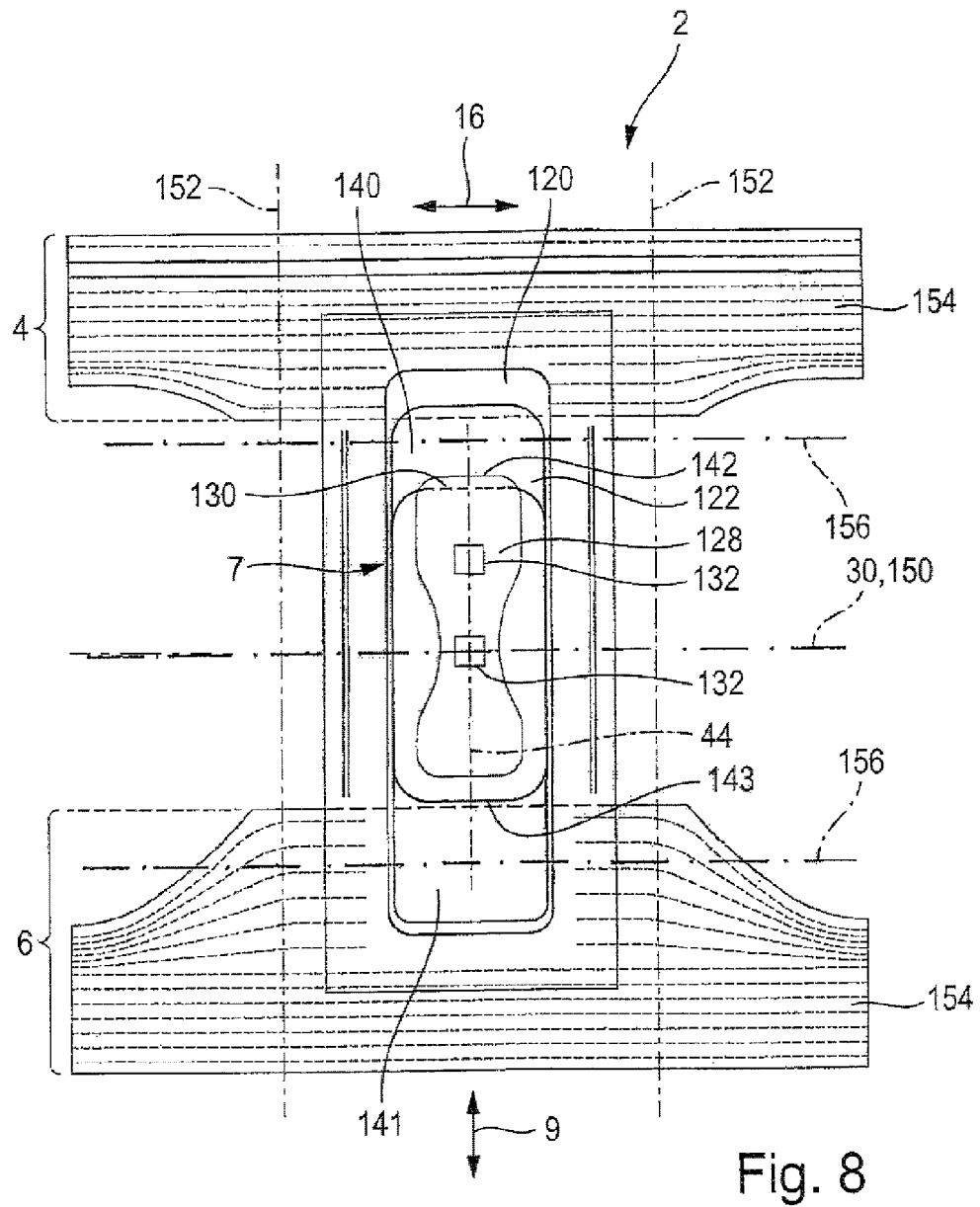
FIG. 8 shows a representation corresponding to FIG. 1, illustrating the construction of the absorption body and the folding axes.

FIGS. 8 and 9 show the construction of the absorption body 7 in a top view and in a sectional view along the longitudinal center axis 44. Starting from its body-averted side, the absorption body 7 includes a basic layer 120 made of cellulosic fiber material with an exemplary mass per area of 176 g/m$^2$. Depending on the exact two-dimensional extent, the basic layer contains 10 to 14 g of cellulosic fiber material.

On the basic layer 120, a absorption body layer 122 is placed, which is three-dimensionally shaped at least with regard to the mass per area of absorption body material. In a center region 124, the absorption body layer 122 has a higher mass per area of absorption body material then in front and rear regions 126, 127, in longitudinal direction 9. In the exemplary shown case, the mass per area of cellulosic fiber material in the front and rear region 126, 127 of the absorption body layer 122 is 162 g/m$^2$ and in the center region 124 329 g/m$^2$. In addition, the absorption body layer 122 includes overall about 7 g of superabsorbent polymer materials, which are homogenously, evenly distributed in the absorption body layer 122. The regions 126, 127 and 124 are offset backward in longitudinal direction 9 relative to the two-dimensional extent of the basic layer 120 as can be seen from FIG. 8.

Finally, the absorption body 7 includes a body-facing liquid-absorption and distribution layer 128, which in the exemplary and preferred shown case has an hour class-shape, and predominantly extends on the center region 124 of the absorption body layer 122. The liquid-absorption and distribution layer 128 protrudes over a stomach-section-side longitudinal end 130 of the center region 124 of the absorption body layer 122. It includes a mass per area of fiber material i.e., in the form of intra-cross-linked cellulose fibers (curled fiber) of for example 149 g/m$^2$ with an overall mass corresponding to the exemplary extent of about 2.8 g.

The basic layer 120, the three regions 124, 126 and 127 of the absorption body layer 122 and the body-facing liquid absorption- and distribution layer 128 have a uniform mass per area of absorption body materials across their two-dimensional extent.

The mass per area is measured as described above by analyzing a test specimen of 25 mm×25 mm, which is punched out through all previously described layers of the absorption body 7. The area 132 (25 mm×25 mm) to be punched out is always centered relative to the longitudinal center axis 44, as indicated in FIG. 8. When the mass per area in longitudinal direction 9 is determined more frontward or more rearward, the test specimen is accordingly centered relative to the longitudinal center axis 44.

It can be seen that the mass per area of absorption body material thus decreases stepwise in the direction toward a stomach-section-side end 134 and in the direction toward a back-section-side end 136 of the absorption body 7. In this way, plateaus 138 are formed between the steps. In the region of these plateaus 138, the mass per area of absorption body material of the layers of the absorption body 7 lying there underneath is preferably but not necessarily, constant.

In the shown preferred embodiment of the incontinence article, the mass per area of the absorption body 7, starting from the transverse center axis 30 anteriorly and posteriorly in the region of the overlap of the body-facing liquid absorption- and distribution layer 128 with the center region 124 of the absorption body layer 122, is essentially constant.

In FIGS. 8 and 9, plateaus 140, 141 can be seen which adjoin a step 142, 143 anteriorly or posteriorly in the longitudinal direction 9. In the region of these plateaus 140, 141, the mass per area of the absorption body 7 is significantly reduced relative to the mass per area in the region of the transverse center axis 30.

In the following, the folding of the incontinence article in pant form for the stacked arrangement of multiple incontinence articles in a packaging for distribution is described by way of the FIGS. 8, 10 and 11: as already mentioned, the transverse center axis 30 forms a first folding axis 150, about which the incontinence article is folded, so that the stomach section 4 and back section 6 can be permanently joined together for forming lateral seam regions 14 i.e., by conventional joining methods, such as gluing, ultrasound etc. Further, second folding lines 152 which approximately extend in longitudinal direction 9 are only outlined in FIG. 8, because the folding does not occur in the stretched out state shown in FIG. 8, but after finishing the pant-shaped incontinence article in the only schematically shown state in FIG. 10 a. Starting from this outlined state shown in FIG. 10 a, regions 154 of the stomach section 4 and back section 6 which laterally extend over the crotch section 8 on both sides, are folded in the direction towards the longitudinal center axis 44, preferably onto the outsides of the stomach section 4, so that the configuration outlined in FIG. 10 b is obtained.

Figure 10A:
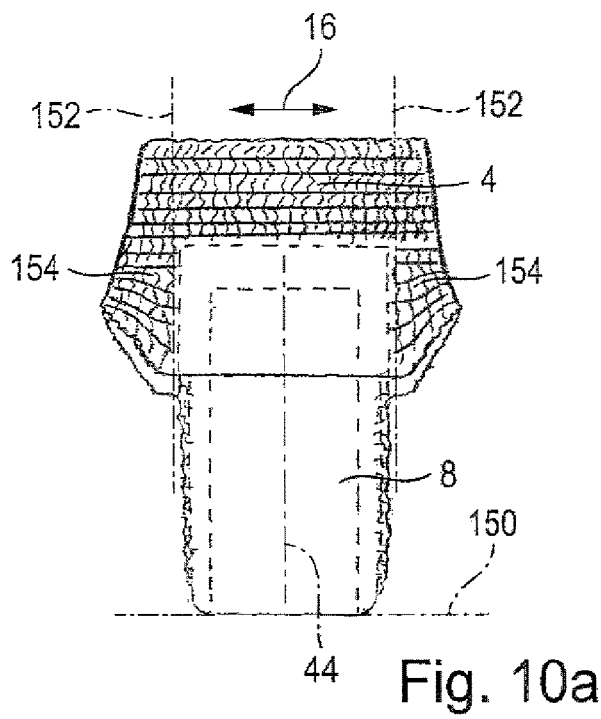
FIGS. 10 a,b,c show three schematic views of the incontinence article, illustrating the folding.
Figure 10B:
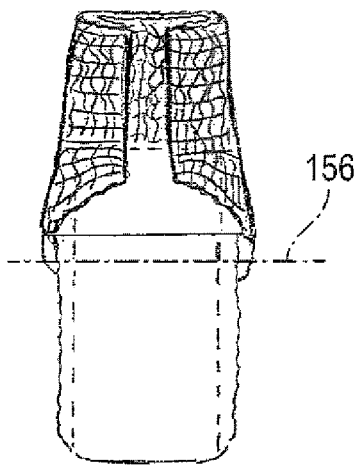
Figure 10C:
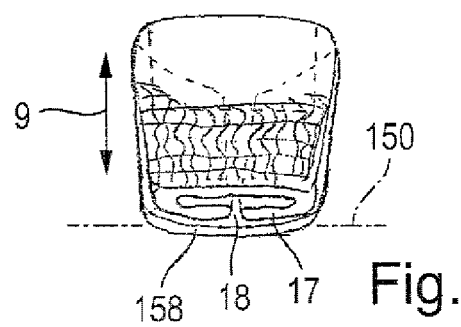

FIGS. 8 and 10 show a third folding axis 156, which extends in transverse direction 16, and whose position relative to the absorption body 7 can be seen from FIG. 8. Further folding about this only further folding axis 156, which extends in transverse direction 16, results in the compactly folded configuration of the pant-shaped incontinence article shown in FIG. 10 c. It can be seen that the border of the stomach and back band 17, which delimits the waist opening 18, does not protrude in longitudinal direction 9 over the outer folding edge 158 of the incontinence article, which folding edge 158 is formed by the first folding axis 150.

Figure 11:
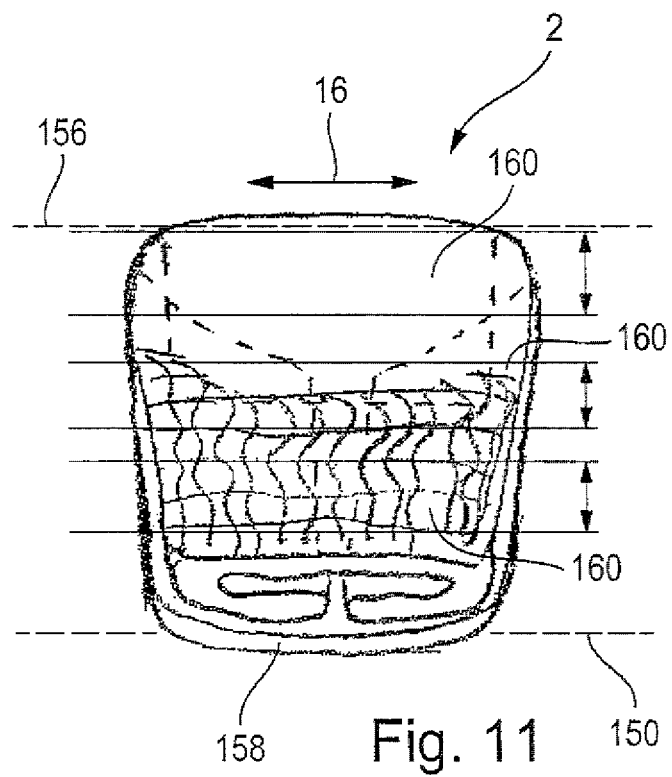
FIG. 11 shows a schematic view of the folded incontinence article, illustrating sampling during determination of the thickness.

FIG. 11 illustrates at which sites the thickness of the incontinence article 2, which is folded into the configuration of FIG. 10 c, is determined. As already mentioned, the entire such folded incontinence article 2 is punched out over the entire transverse direction 16 with a punching knife at a distance of about 10 mm to the folding edges or folding axes 150 and 156, thereby forming strip-shaped test specimens 160. Based on these test specimens 160, which include all layers of the incontinence article, the thickness is then determined as described above.

While the invention has been illustrated and described in connection with currently preferred embodiments shown and described in detail, it is not intended to be limited to the details shown since various modifications and structural changes may be made without departing in any way from the spirit of the present invention. The embodiments were chosen and described in order to best explain the principles of the invention and practical application to thereby enable a person skilled in the art to best utilize the invention and various embodiments with various modifications as are suited to the particular use contemplated.

What is claimed as new and desired to be protected by Letters Patent is set forth in the appended claims and includes equivalents of the elements recited therein:

1. An incontinence article in pant form for absorbing bodily excretions, comprising:
    a stomach section;
    a back section, spaced apart from the stomach section in a longitudinal direction of the incontinence article along a longitudinal center axis, said stomach section and back section having respective lateral seam regions and being joined at the respective lateral seam regions to form respective lateral seams extending in the longitudinal direction thereby forming a stomach- and back band which is continuous in a transverse direction of the incontinence article, and has a circumferentially closed waist opening;
    a crotch section having an absorption body and a body-averted side and extending in the longitudinal direction between the stomach section and the back section, said crotch section overlapping with the stomach section and the back section in respective overlapping regions and being non-detachably connected with the body-averted side to the stomach section and to the back section in the respective overlapping regions, said stomach section, back section and crotch section together delimiting leg openings of the incontinence article, said stomach and back section having respective crotch-side regions facing the leg openings;
    first elastifying means extending in spaced apart and parallel relationship to one another in the transverse direction in the stomach section and back section, thereby two-dimensionally elastifying the stomach section and the back section; and
    second elastifying means extending in the respective crotch-side regions of the stomach and back sections, from the respective lateral seam regions towards the longitudinal center axis into the respective overlapping regions of the crotch section and back section and of the crotch section and stomach section in an arched course with increasing distance to one another,
    wherein an extent of the respective lateral seams in the longitudinal direction is 100-170 mm, and wherein a ratio between the extent of the respective lateral seams in longitudinal direction and an extent of the incontinence article between a waist border of the stomach- and back band and a transverse center axis of the incontinence article is at most 0.42,
    wherein in the stomach section and in the back section a ratio between a distance of an outermost, waist-facing one of the first elastifying means in the longitudinal direction to an innermost, crotch-facing one of the first elastifying means and the extent of the incontinence article between a border of the waistband and the transverse center axis is at most 0.3,
    wherein the first elastifying means have a distance to one another which is at least 20% greater than a distance between the second elastifying means to one another defined in the lateral seam region,
    wherein the first elastifying means have a thread strength which is at least 20% greater than a thread strength of the second elastifying means,
    wherein the first and second elastifying means are fixed in the stomach section and in the back section with a pre-tension, and wherein the pre-tension of the first elastifying means is at least 10% greater than the pretension of the second elastifying means.

2. The incontinence article of claim 1, wherein the second elastifying means have no elastifying effect in the respective overlapping regions, or are cut in the respective overlapping regions.

3. The incontinence article of claim 1, wherein the ratio between the extent of the respective lateral seams in the longitudinal direction and the extent of the incontinence article between the waist border of the stomach- and back band and the transverse center axis of the incontinence article is at most 0.4.

4. The incontinence article of claim 1, wherein in the stomach section and in the back section the ratio between the distance of the outermost waist-facing first elastifying means in longitudinal direction from the innermost crotch-facing first elastifying means and the extent of the incontinence article between the border of the waistband and the transverse center axis is at most 0.29.

5. The incontinence article of claim 1, wherein in the stomach section and in the back section the distance of the outermost waist-facing first elastifying means in longitudinal direction to the innermost waist facing first elastifying means is at most 120 mm.

6. The incontinence article of claim 1, wherein a maximal extent of the stomach section in the longitudinal direction is 135-260 mm and/or the maximal extent of the back section in longitudinal direction is 200-320 mm.

7. The incontinence article of claim 1, wherein a minimal distance of the stomach section and the back section to each other in the longitudinal direction is 250-400 mm.

8. The incontinence article of claim 1, wherein a ratio between the extent of the respective lateral seams in the longitudinal direction and the extent of the stomach section or back section in the transverse direction is at most 0.22.

9. The incontinence article of claim 1, wherein in the stomach section and in the back section a ratio between the distance of the outermost waist-facing first elastifying means in the longitudinal direction from the innermost crotch-facing first elastifying means and an extent of the stomach section or the back section in the transverse direction is at most 0.15.

10. The incontinence article of claim 1, wherein in the stomach section and/or in the back section, a ratio between the distance of the first elastifying means in the longitudinal direction to one another and the distance of the outermost waist-facing first elastifying means in the longitudinal direction to the innermost crotch-facing first elastifying means is between 0.08 and 0.25.

11. The incontinence article of claim 1, wherein the distance of the first elastifying means in the longitudinal direction to each other is at least 8 mm.

12. The incontinence article of claim 1, wherein the first elastifying means are spaced apart by a distance, which is at least 30% greater than the distance defined in the respective lateral seam regions of the second elastifying means to each other.

13. The incontinence article of claim 1, wherein a minimal distance of the second elastifying means to each other in the respective lateral seam regions is 3-8 mm.

14. The incontinence article of claim 1, wherein the thread strength of the first elastifying means is greater than the thread strength of the second elastifying means by at least 30%.

15. The incontinence article of claim 1, wherein the thread strength of the first elastifying means is at least 1000 dtex.

16. The incontinence article of claim 1, wherein the thread strength of the second elastifying means is 500-1100 dtex.

17. The incontinence article of claim 1, wherein the pretension of the first elastifying means is greater than the pretension of the second elastifying means by at least 30%.

18. The incontinence article of claim 1, wherein the pretension of the first elastifying means is 3-8.

19. The incontinence article of claim 1, wherein the pretension of the second elastifying means is 2-5.

20. The incontinence article of claim 1, wherein the second elastifying means are arranged and fixed between a first chassis material layer which forms a visible side of the stomach section or the back section, and a second chassis material layer lies inwardly relative to the first chassis material layer, wherein the second chassis material layer in the longitudinal direction of the incontinence article does not extend past a respective associated one of the overlapping regions of the crotch section and stomach section or crotch section and back section.

21. The incontinence article of claim 1, wherein the second elastifying means are fixed in a glue bed between chassis material layers of the incontinence article, and/or wherein the first elastifying means are fixed between the chassis material layers by an adhesive provided in single-strand application on the first elastifying means.

22. The incontinence article of claim 1, wherein the first elastifying means in the stomach section and in the back section are fixed between a body-averted chassis material layer and a body-facing chassis material layer by an adhesive provided in single-strand application on the elastifying means, and wherein the body-facing chassis material layer protrudes over an associated end of the crotch section on a body-facing side of the crotch section.

23. The incontinence article of claim 1, wherein the first elastifying means in the stomach section and the back section are fixed between a body-averted chassis material layer and a body-facing chassis material layer by an adhesive provided in single-strand application on the elastifying means, wherein on the border of the stomach- and back band the chassis material layers are not folded about one another, and wherein the body-facing chassis material layer and the body-averted chassis material layer along the waist opening on the border of the stomach- and back band are not fixed to one another, thereby respectively forming a freely ending waist-side border section.

24. The incontinence article of claim 1, wherein a surface over which the crotch section and the stomach section overlap in the respective overlapping region is at least 20% and/or wherein a surface over which the crotch section and the back section overlap in the respective overlapping region is at least 25.

\* \* \* \* \*